US00PP27553P2

(12) United States Plant Patent
Green, Jr.

(10) Patent No.: US PP27,553 P2
(45) Date of Patent: Jan. 17, 2017

(54) ***CAMELLIA* PLANT NAMED 'GREEN 02-004'**

(50) Latin Name: *Camellia sasanqua*
Varietal Denomination: Green 02-004

(71) Applicant: Robert M. Green, Jr., Fairhope, AL (US)

(72) Inventor: Robert M. Green, Jr., Fairhope, AL (US)

( * ) Notice: Subject to any disclaimer, the term of this patent is extended or adjusted under 35 U.S.C. 154(b) by 0 days.

(21) Appl. No.: 14/756,160

(22) Filed: Aug. 10, 2015

(51) Int. Cl.
*A01H 5/00* (2006.01)

(52) U.S. Cl.
USPC ..... Plt./243

(58) Field of Classification Search
USPC ..... Plt./243
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Camellia sasanqua* named 'Green 02-004', that is characterized by its compact, dense, and rounded plant habit, its dark green foliage, its double flowers that are white in color, its very floriferous and long-lasting bloom habit, and its resistance to root rot (*Phytophora cinnamomi*) and dieback (*Glomerella cingulata*).

2 Drawing Sheets

Botanical classification: *Camellia sasanqua.*
Variety denomination: 'Green 02-004'.

BACKGROUND OF THE INVENTION

The present invention relates to a new and distinct cultivar of *Camellia* plant, botanically known as *Camellia sasanqua*, 'Green 02-004'. The new cultivar will be referred to hereafter by its cultivar name, 'Green 02-004'. 'Green 02-004' is a new perennial shrub grown for container and landscape use.

'Green 02-004' was derived from an ongoing breeding program conducted by the Inventor in Fairhope, Ala., USA since 1992. The objectives of the breeding program are to develop new cultivars of *Camellia sasanqua* with compact plant habits, vigorous growth habits, improved disease resistance, and extended bloom periods. 'Green 02-004' originated as a seedling that arose from seed planted from open pollination of the *Camellia sasanqua* cultivar 'Shishi Gashira' (not patented) as the female parent in 2000 in Fairhope, Ala. The male parent is unknown. The new *Camellia* was selected as a single unique plant in Fall of 2004.

Asexual reproduction of the new cultivar was first accomplished by stem cuttings by the Inventor in 2004 in Fairhope, Ala. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia*. These attributes in combination distinguish 'Green 02-004' as a new and distinct cultivar of *Camellia.*

1. 'Green 02-004' exhibits a compact, dense, and rounded plant habit.
2. 'Green 02-004' exhibits dark green foliage.

3. 'Green 02-004' exhibits double flowers that are white in color.
4. 'Green 02-004' exhibits a very floriferous and long-lasting bloom habit.
5. 'Green 02-004' exhibits resistance to root rot (*Phytophora cinnamomi*) and dieback (*Glomerella cingulata*).

The female parent of 'Green 02-004', 'Shishi Gashira', differs from 'Green 02-004' in having flowers with fewer petals that are rose pink in color and in having flowers that are more asymetrically semi-double in form. 'Green 02-004' can also be compared to the *Camellia* cultivars 'Green 94-010' (U.S. Plant Pat. No. 20,454) and 'Snow Flurry' (not patented). Both culivars are similar to 'Green 02-004' in having flowers that are white in color. 'Green 94-010' differs from 'Green 02-004' in having a less compact plant habit and in having a shorter bloom season. 'Snow Flurry' differs from 'Green 02-004' in having an open plant habit, in having leaves that are lighter in color, in having a less uniform growth habit, and in having a shorter bloom season.

BRIEF DESCRIPTION OF THE DRAWINGS

The accompanying colored photographs illustrate the overall appearance and distinct characteristics of the new *Camellia*. The photographs were taken of a 32 month-old plant of 'Green 02-004', as grown outdoors in a trial garden in Fairhope, Ala.

The photograph in FIG. 1 provides a side-view of the plant habit of 'Green 02-004'.

Figure 1:
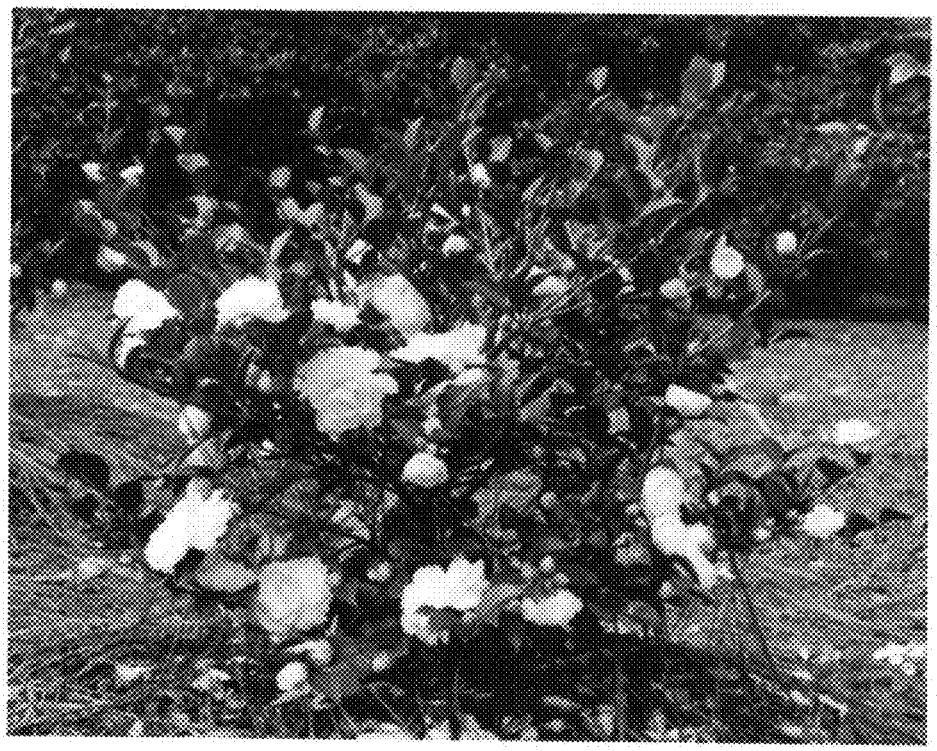
Figure 2:
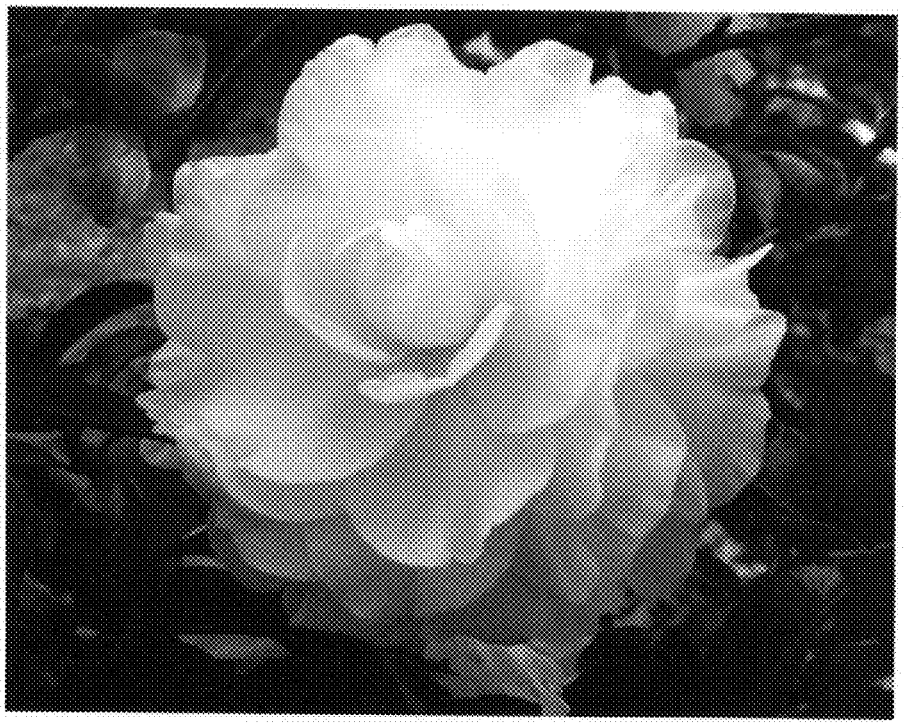

The photograph in FIG. 2 provides a close-up view of a flower of 'Green 02-004'.

Figure 3:
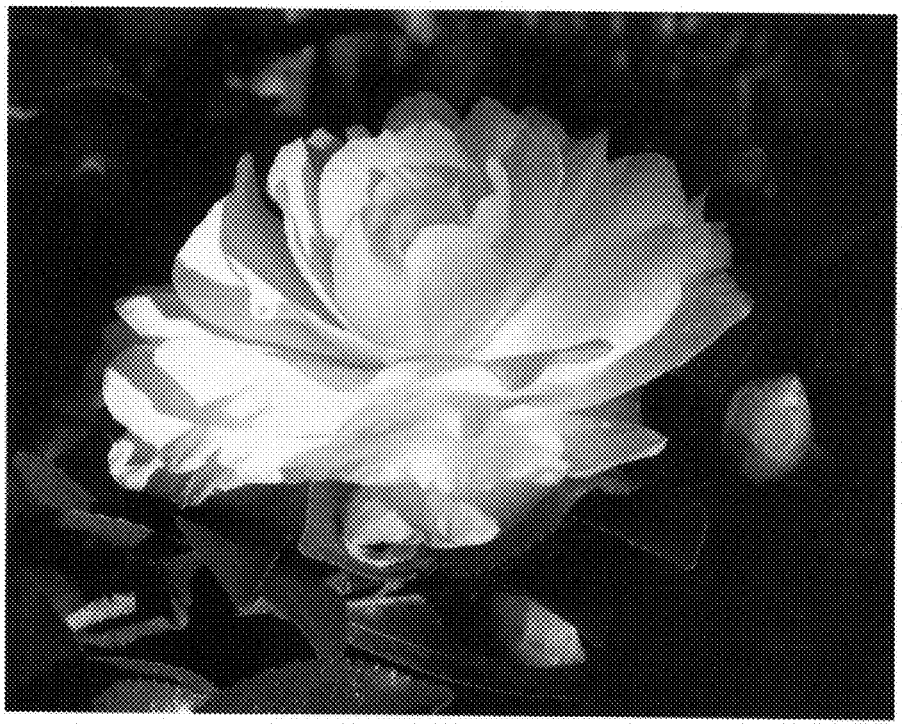

The photograph in FIG. 3 provides a close-up view of the buds and a flower of 'Green 02-004'.

The colors in the photographs are as close as possible with digital photography techniques available, the color values cited in the detailed botanical description accurately describe the colors of the new *Camellia.*

DETAILED BOTANICAL DESCRIPTION

The following is a detailed description of three year-old plants of the new cultivar as grown ourtdoors in three-gallon containers in Fairhope, Ala. Plants were grown under 30% shade cloth with average day temperatures between 10 to 24° C. (50 to 75° F.) and average night temperatures between −1 to 10° C. (30 to 50° F.). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—October to January in Fairhope, Ala.

*Plant type.*—Evergreen shrub.

*Plant habit.*—Compact, dense and rounded.

*Height and spread.*—An average of 1.2 m in height and spread.

*Cold hardiness.*—At least hardy in U.S.D.A. Zones 7 to 9.

*Diseases and pests.*—Has shown resistance to root rot (*Phytophora cinnamomi*) and dieback (*Glomerella cingulata*).

*Propagation.*—Stem cuttings.

*Time required for root initiation.*—An average of 40 days.

*Time required for root development.*—About 6 months to fully develop in a 3 inch container.

*Growth rate.*—Moderate.

Branch description:

*Stem shape.*—Round.

*Stem strength.*—Strong.

*Stem color.*—Young; 165A, mature bark; 200C to 200D suffused with 165A at the base becoming 165B towards the middle and apex.

*Stem size.*—An average of 41 to 46 cm in length and 2 mm in width.

*Stem surface.*—Young; bark-like, slightly glossy and sparsely covered with soft pubescent hairs an average of 0.5 mm in length and 165A in color, mature; bark-like, slightly rough to touch.

*Branching.*—Densely branched with an average of 15 main lateral branches and 12 to 18 secondary lateral branches per main laterals.

Foliage description:

*Leaf shape.*—Ovate.

*Leaf division.*—Simple.

*Leaf base.*—Rounded and cuneate.

*Leaf apex.*—Acuminate and obtuse.

*Leaf fragrance.*—None.

*Leaf margins.*—Serrate.

*Leaf arrangement.*—Alternate.

*Leaf attachment.*—Petiolate.

*Leaf substance.*—Young leaves; thick and rubbery, mature leaves; thick.

*Leaf surface.*—Upper surface; smooth, glabrous, and very glossy, lower surface; smooth, glabrous, satiny, and sparsely pubescent on first year growth.

*Leaf size.*—An average of 4 cm in length and 2.5 cm in width.

*Leaf quantity.*—An average of 10 per branch 20 cm in length.

*Leaf venation.*—Pinnate, inconspicuous except mid rib; upper surface 144A in color, lower surface a blend between 143A and 144A.

*Leaf color.*—Young and mature leaves upper surface; a blend between 139A and 136A, young and mature leaves lower surface; 137A.

*Petioles.*—Flattened oblique in shape, an average of 2 mm in width and 5 mm in length, glabrous surface, 144A in color.

*Stipules.*—None.

Inflorescence description:

*Inflorescence type.*—Single, rotate, double flowers.

*Flower number.*—An average of 4 to 5 per lateral stem.

*Flower fragrance.*—Slightly fragrant.

*Flower longevity.*—About one week, self cleaning.

*Flower type.*—Solitary, double.

*Flower aspect.*—Outward to slightly upright, held at an average angle of 45° from stem.

*Flower size.*—An average of 7.6 cm in diameter and 2.5 cm in depth.

*Peduncles.*—None, flowers are sessile to stem.

*Flower buds.*—Ovoid in shape, an average of 2 cm in length and 1.5 cm in width, color; 144B, with 68A at the apex.

*Sepals.*—An average of 6, ovate to rounded in shape and strongly cupped inward, imbricate, an average of 1.2 cm in length and 1 cm in width, obtuse apex, truncate base, entire margin, color; upper and lower surface 145B with base 144A and margins 200B, mid rib; upper surface covered with silky hairs and average of 0.5 mm in length, lower surface glabrous and satiny.

*Petals.*—40 to 48, oblong to cordate in shape, upper and lower surface; glabrous and dull, entire margin, cordate apex, convexly cuneate base, an average of 3.0 cm in length and 2.3 cm in width, color; upper and lower surfaces when opening; 157C, upper and lower surfaces when fully open a blend of 155C and N155D.

Reproductive organs:

*Pistil.*—None observed.

*Stamens.*—Few, sparse, and petal-like with mal-formed anthers an average of 6.5 mm in length, 160A to 160B in color, no pollen detected.

*Fruit and seed.*—Not present.

It is claimed:

1. A new and distinct cultivar of *Camellia* plant named 'Green 02-004' as herein illustrated and described.

* * * * *